United States Patent
Guo et al.

(10) Patent No.: US 12,175,675 B1
(45) Date of Patent: Dec. 24, 2024

(54) IMAGE PROCESSING METHOD AND SYSTEM FOR IMPROVING THREE-DIMENSIONAL DISPLAY EFFECT OF BLOOD VESSELS

(71) Applicant: Shenyang university of technology, Shenyang (CN)

(72) Inventors: Hongyu Guo, Shenyang (CN); Ying Wang, Shenyang (CN)

(73) Assignee: SHENYANG UNIVERSITY OF TECHNOLOGY, Shenyang (CN)

( * ) Notice: Subject to any disclaimer, the term of this patent is extended or adjusted under 35 U.S.C. 154(b) by 0 days.

(21) Appl. No.: 18/675,741

(22) Filed: May 28, 2024

(30) Foreign Application Priority Data

May 29, 2023 (CN) .......................... 202310612282.X

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/20076* (2013.01); *G06T 2207/20182* (2013.01); *G06T 2207/30101* (2013.01)

(58) Field of Classification Search
CPC ......... G06T 7/0012; G06T 2207/20076; G06T 2207/20182; G06T 2207/30101; G06T 2207/10088; G06T 2207/10081; G06T 2207/30104; G06T 2200/04; G06T 11/005; G06T 5/00; G16H 30/40
See application file for complete search history.

(56) References Cited

U.S. PATENT DOCUMENTS

2022/0164967 A1* 5/2022 Jia .......................... G06T 17/00

OTHER PUBLICATIONS

Jin et al. MR Venography of the Brain With EnhancedVessel Contrast Using Image-Domain High-PassFiltering of the Susceptibility Phase Shift (Year: 2011).*
Yiping P. Du et.al, Vessel Enhancement Filtering in Three-Dimensional MR Angiograms—Using Long-Range Signal Correlation, Journal of Magnetic Resonance Imaging, Apr. 30, 1997, pp. 447-450.
Fan Huang et.al, Vascular biomarkers for diabetes and diabetic retinopathy screening, Computational Retinal Image Analysis, Dec. 31, 2019, pp. 319-326.

(Continued)

*Primary Examiner* — Andrew W Bee
*Assistant Examiner* — Winta Gebreslassie
(74) *Attorney, Agent, or Firm* — Hemisphere Law, PLLC; Zhigang Ma

(57) ABSTRACT

According to an image processing method and system for improving three-dimensional display effect of blood vessels provided by the present invention, the image processing method comprises the following steps: design an interpolation algorithm to preprocess the original data to obtain a preprocessed image based on the original image volume data before projection; determine the blood vessel trend according to the preprocessed image, eliminate isolated points, and perform image smoothing processing on the blood vessel trend to obtain a smooth image; and process the smooth image by a nonlinear change method to perform nonlinear enhanced display of blood vessels and suppress the background. And improve the display effect of blood vessel signals.

4 Claims, 4 Drawing Sheets

(56) References Cited

OTHER PUBLICATIONS

Mehran Moshfeghi, Directional Interpolation for Magnetic Resonance Angiography Data, IEEE Transactions on Medical Imaging, Jun. 30, 1993, pp. 366-379, vol. 12, issue 2.

CNIPA, Notification of First Office Action for CN202310612282.X, Nov. 16, 2023.

Shenyang University of Technology (Applicant), Reply to Notification of First Office Action for CN202310612282.X, w/ replacement claims, Dec. 28, 2023.

Shenyang University of Technology (Applicant), Supplemental Reply to Notification of First Office Action for CN202310612282.X, w/ (allowed) replacement claims, Feb. 19, 2024.

CNIPA, Notification to grant patent right for invention in CN202310612282.X, Feb. 26, 2024.

\* cited by examiner

Design an interpolation algorithm to preprocess the original data to obtain a preprocessed image based on the original image volume data before projection.

Determine the blood vessel trend according to the preprocessed image, eliminate isolated points, and perform image smoothing processing on the blood vessel trend to obtain a smooth image.

Process the smooth image by a nonlinear change method to perform nonlinear enhanced display of blood vessels and suppress the background.

FIG. 1

IMAGE PROCESSING METHOD AND SYSTEM FOR IMPROVING THREE-DIMENSIONAL DISPLAY EFFECT OF BLOOD VESSELS

TECHNICAL FIELD

The invention relates to the field of image processing, in particular to an image processing method and system for improving three-dimensional display effect of blood vessels.

BACKGROUND

In medical imaging, such as CT and MRI, in order to obtain 3D images of blood vessels from 2D tomography images, the characteristics of blood vessel branches trend, the degree of blood vessel stenosis and blood vessel symmetry can be observed as a whole, and then they are used to diagnose diseases such as blood vessel stenosis, cerebral aneurysm and blood vessel malformation. There are many scanning methods to obtain blood vessel images, such as TOF MIRA, PCA and CTA. Based on the characteristics that the overall performance of the blood vessel signal is the brightest signal (or dark signal) in all layers of images, MIP is often used in image post-processing technology to display blood vessels in 3D. However, due to the quality of the collected multi-layer 2D images and MIP algorithm, there will be some problems in the 3D images after MIP, such as discontinuous blood vessels, uneven blood vessel signals and unclear blood vessel display with strong background signals. The overall display effect of blood vessels can be improved by necessary post-processing the acquired 2D images and 3D volume data composed of multi-layer 2D images.

Maximum intensity projection (MIP) is one of the most common 3D image display methods. Light is projected along a certain direction. When the light beam passes through a 2D original image of a section of tissue with multiple layers, the pixels with the highest density in the image are retained and projected onto a 2D plane, thus forming a MIP reconstructed image. For example, a ray of light is emitted from the slice direction from back to front and projected on a two-dimensional plane, and the maximum pixel value that the light passes through is the pixel value of the image on the two-dimensional plane, that is to say that it is a projection reconstruction image in the slice direction. It is conceivable that if the slice images of multi-layer blood vessels are reconstructed by projection from all directions, the angiographic images in all directions will be obtained.

SUMMARY

In view of the above problems, the present invention has been put forward in order to provide an image processing method and system for improving three-dimensional display effect of blood vessels to overcome or at least partially solve the above problems.

According to one aspect of the present invention, an image processing method for improving three-dimensional display effect of blood vessels is provided, and the image processing method comprises the following steps:

design an interpolation algorithm to preprocess the original data to obtain a preprocessed image based on the original image volume data before projection;

determine the blood vessel trend according to the preprocessed image, eliminate isolated points, and perform image smoothing processing on the blood vessel trend to obtain a smooth image;

and process the smooth image by a nonlinear change method to perform nonlinear enhanced display of blood vessels and suppress the background.

Optionally, the step of designing an interpolation algorithm to preprocess the original data based on the original image volume data before projection specifically includes the following steps: interpolate the original image volume data into data with the same resolution in the layer direction, the row direction and the column direction.

Optionally, the step of designing an interpolation algorithm to preprocess the original data based on the original image volume data before projection specifically includes the following steps:

respectively calculate that resolution of the original image volume data in three directions of row, column and layer;

judge whether to interpolate according to the actual resolutions of the original image volume data in three directions, and if so, select an appropriate interpolation direction and interpolation algorithm to preprocess the original image volume data.

Optionally, the interpolation algorithm includes linear interpolation and cubic spline interpolation.

Optionally, determine the blood vessel trend according to the preprocessed image, and eliminate isolated points, which specifically includes the following steps:

circulate each point in the preprocessed image, and judge whether the points to be identified are abnormal noise points one by one along three principal axes;

judge whether it is an abnormal point or not, and corresponding point is the abnormal point if the pixel value of the corresponding point is larger than the values of six adjacent points in three directions around X, Y, and Z, and filter out the abnormal point;

for each voxel, the vector formed with the surrounding 26 points is calculated to form the direction of blood vessel trend;

in the 13 directions of blood vessel trend, use the points in the two nearest neighbors to average respectively, so as to obtain 13 candidate values;

use the maximum of 13 candidate values as the value of the point to be filtered, then the filtering is completed.

Optionally, perform image smoothing processing on the blood vessel trend to obtain a smooth image, which specifically includes the following steps:

judge the direction of the candidate blood vessel trend, and decide which direction is the most possible blood vessel trend;

traverse the direction of 13 blood vessel trend and calculate the absolute value err of each direction;

compare the absolute value err values in 13 directions, select the direction with the smallest absolute value err as the most possible blood vessel direction, and replace the value of the corresponding point with the average value my value in the corresponding direction to complete the smoothing function.

Optionally, traverse the direction of 13 blood vessel trend and calculate the absolute value err of each direction, which specifically includes the following steps:

calculate the average value my of the corresponding point and two neighboring points in the direction of a certain blood vessel trend;

calculate the absolute value of the difference between the corresponding point and the average value, which is the first absolute value err1 of the difference;

calculate the absolute value of the difference between two neighboring points, which is the second absolute value err2;

calculate the sum absolute value err of the first difference absolute value err1 and the second difference absolute value err2.

Optionally, the step of processing the smooth image by a nonlinear change method to perform nonlinear enhanced display of blood vessels and suppress the background specifically includes the following steps:

the formula of nonlinear transformation adopts gamma transformation, and the formula is as follows: $S=I^\gamma$ wherein, $\gamma>1$;

wherein, S is the transformed image, $\gamma$ is the variable that controls the transformation effect, and it is used to compress the background dark signal, and the larger $\gamma$ is, the more obvious the effect is;

or use the improved gamma transformation, the formula is $S=(1-\alpha I+\exp(-I)))^\gamma$, where S is the transformed image, I is the original image, $\alpha$ and $\gamma$ are the control variables, and the value of $\alpha$ less than 1 is selected; and $\gamma$ is greater than 1.

The present invention also provides an image processing system for improving three-dimensional display effect of blood vessels, and the image processing method for improving three-dimensional display effect of blood vessels is applied, wherein, the processing system comprises:

an interpolation module, which is used for designing an interpolation algorithm to preprocess the original data to obtain a preprocessed image based on the original image volume data before projection;

a filtering and smoothing module, which is used for determining the blood vessel trend according to the preprocessed image, eliminating isolated points, and performing image smoothing processing on the blood vessel trend to obtain a smooth image;

and a background suppression module, which is used for processing the smooth image by a nonlinear change method to perform nonlinear enhanced display of blood vessels and suppress the background.

According to the image processing method and system for improving three-dimensional display effect of blood vessels provided by the present invention, the image processing method comprises the following steps: design an interpolation algorithm to preprocess the original data to obtain a preprocessed image based on the original image volume data before projection; determine the blood vessel trend according to the preprocessed image, eliminate isolated points, and perform image smoothing processing on the blood vessel trend to obtain a smooth image; and process the smooth image by a nonlinear change method to perform nonlinear enhanced display of blood vessels and suppress the background. And improve the display effect of blood vessel signals.

The above description is only an overview of the technical scheme of the present invention, which can be implemented according to the contents of the specification in order to clearly understand the technical means of the present invention, and in order to make the above and other purposes, features and advantages of the present invention more obvious and understandable, the following is a specific embodiment of the present invention.

BRIEF DESCRIPTION OF DRAWINGS

In order to explain the technical scheme of the embodiment of the present invention more clearly, the drawings needed in the description of the embodiment will be briefly introduced below. Obviously, the drawings in the following description are only some embodiments of the present invention. For ordinary people in the field, other drawings can be obtained according to these drawings without creative work.

FIG. 1 is a flowchart of an image processing method for improving three-dimensional display effect of blood vessels provided by the embodiment of the present invention;

DETAILED DESCRIPTION OF EMBODIMENTS

Figure 2:
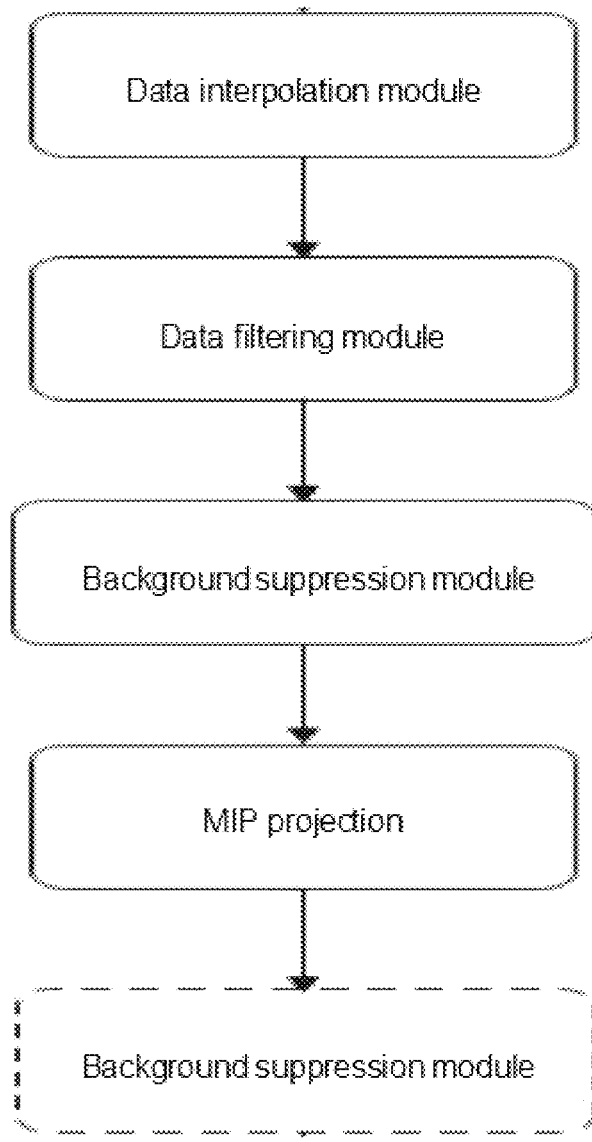
FIG. 2 is a block diagram of an image processing system for improving three-dimensional display effect of blood vessels provided by an embodiment of the present invention.

Exemplary embodiments of the present disclosure will be described in more detail below with reference to the accompanying drawings. Although exemplary embodiments of the present disclosure are shown in the drawings, it should be understood that the present disclosure can be implemented in various forms and should not be limited by the embodiments set forth herein. On the contrary, these embodiments are provided for a more thorough understanding of the disclosure, and will fully convey the scope of the disclosure to those skilled in the field.

The terms "include" and "have" in the description, claims and drawings of the present invention, as well as any variations thereof, are intended to cover non-exclusive inclusion, for example, including a series of steps or units.

In the following, the technical scheme of the present invention will be further described in detail with the attached drawings and embodiments.

As shown in FIG. 1, the image processing method for improving three-dimensional display effect of blood vessels is provided, and the image processing method comprises the following steps:

design an interpolation algorithm to preprocess the original data to obtain a preprocessed image based on the original image volume data before projection; and improve the display effect of 3D images;

determine the blood vessel trend according to the preprocessed image, eliminate isolated points, and perform image smoothing processing on the blood vessel trend to obtain a smooth image; and improve the continuity of blood vessels and the sharpness of blood vessel edges;

and process the smooth image by a nonlinear change method to perform nonlinear enhanced display of blood vessels, improve the uniformity of blood vessel signals, suppress the background and improve the display effect of blood vessel signals.

As shown in FIG. 2, the image processing system for improving three-dimensional display effect of blood vessels comprises: an interpolation module, which is used for designing an interpolation algorithm to preprocess the original data to obtain a preprocessed image based on the original image volume data before projection;

a filtering and smoothing module, which is used for determining the blood vessel trend according to the preprocessed image, eliminating isolated points, and performing image smoothing processing on the blood vessel trend to obtain a smooth image;

and a background suppression module, which is used for processing the smooth image by a nonlinear change method to perform nonlinear enhanced display of blood vessels and suppress the background.

In order to ensure the isotropy of volume data, it is necessary to preprocess the original data and interpolate the original data into data with the same resolution in the layer direction, row direction and column direction.

The specific implementation steps include: it is necessary to calculate the resolution of volume data in three directions: row, column and layer;

according to the actual resolution of image data in three directions, judge whether to interpolate, and choose the appropriate interpolation direction and interpolation algorithm (including linear interpolation and cubic spline interpolation); for example, the interpolation process in Z direction is as follows:

enlarge the size of the original data in the Z direction by 2 times, that is, increase the number of layers by 2 times;

the data of the original layer remains the original data, while the data of the new level is set to 0;

Z-direction interpolation: for each point to be interpolated, use the improved Catmull-Rom spline interpolation algorithm or cubic spline interpolation algorithm to interpolate and calculate the pixel value of the point to be interpolated. The formula of the improved Catmull-Rom spline is as follows:

$$P=((P1+P2)*9-(P0+P3)+8)/16$$

Figure 3:
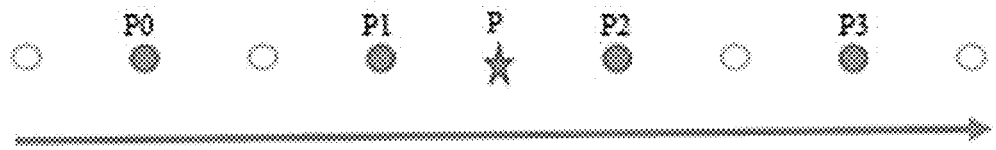
FIG. 3 is a schematic diagram of points and neighboring points during interpolation provided by the embodiment of the present invention, where circular real points are collected points, circular empty points are neighboring points to be interpolated, and triangles are current points to be interpolated.

Among them, P0, P1, P2 and P3 respectively represent the pixel values of four known points adjacent to the point P to be interpolated in the Z direction, and the distribution of neighboring points, as shown in FIG. 3.

Update the resolution in three directions.

And the filtering and smoothing module is used for eliminating abnormal noise points on the original image and smoothing blood vessels.

Figure 4:
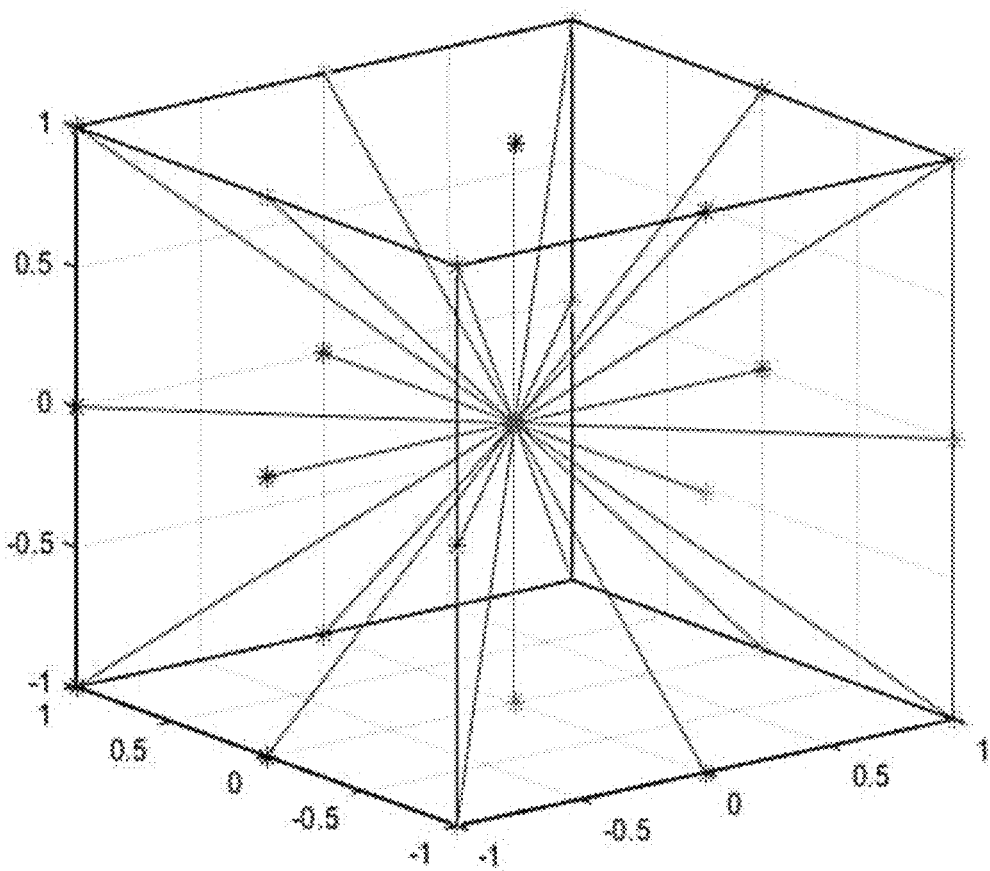
FIG. 4 is a schematic diagram of the possible trends connection of blood vessels formed by points and surrounding points provided by the embodiment of the present invention.

Identify abnormal bright spots and eliminate them. In order to reduce the interference of noise points (that is, non-vascular signals) on subsequent 3D reconstruction, it is necessary to identify these noise points and remove them. The specific method is: circulate each point in the volume data, and judge whether the point to be identified is an abnormal noise point one by one along the three principal axes. The specific methods are as follows: 1) judge whether it is an abnormal point. If the pixel value of that point is larger than the values of the six adjacent points in the three directions of X, Y and Z, it is considered as an abnormal point and needs to be filtered out; 2) for each voxel, calculate the vector formed by it and the surrounding 26 points to form the trend of blood vessels, as shown in FIG. 4. Then, 13 candidate values are obtained by averaging the points in the two nearest neighbors in 13 directions of blood vessel trend. Finally, the maximum of these 13 candidate values is used as the value of the point to be filtered, and the filtering is completed.

Smoothing the pixels along the blood vessel trend to improve the continuity of blood vessels; the specific method is to judge the candidate blood vessel direction and decide which direction is the most possible blood vessel trend direction. Judgment method: traverse 13 blood vessel trend directions: 1) calculate the average value my of this point and its two neighboring points in a certain blood vessel direction; 2) calculate the absolute value err1 of the difference between this point and the average value; 3) calculate the absolute value err2 of the difference between two neighboring points; 4) calculate the sum err of err1 and err2;

Compare the err values in 13 directions, the direction with the smallest err is selected as the most possible blood vessel direction, and the my value in this direction is used to replace the value of this point to complete the smoothing effect.

Background suppression module: nonlinear transformation method is applied to enhance the display of blood vessels and suppress the background. Through this module, the background signal in the blood vessel volume data can be reduced and the blood vessel bright signal can be enhanced.

The formula of nonlinear transformation adopts gamma transformation, and the formula is $S=I^{\gamma}$, ($\gamma>1$) where S is the transformed image and $\gamma$ is the variable that controls the transformation effect. In the present invention, it is greater than 1, such as 1.2, which is used to compress the background dark signal and improve the blood vessel bright signal, and the greater $\gamma$ is, the more obvious the effect is; the improved gamma transform is also used, and the formula is $S=(1-\alpha I+\exp(-I)))^{\gamma}$, where S is the transformed image, I is the original image, $\alpha$ and $\gamma$ are the control variables, and the value of a less than 1 is selected, such as 0.3; $\gamma$ is greater than 1, such as 1.2. The background suppression module is used for the image after MIP.

The beneficial effects: it can improve the display effect of blood vessel signals.

The above specific embodiments have further explained the purpose, technical scheme and beneficial effects of the present invention in detail. It should be understood that the above are only specific embodiments of the present invention and are not used to limit the protection scope of the present invention. Any modification, equivalent substitution, improvement, etc. made within the spirit and principle of the present invention should be included in the protection scope of the present invention.

What is claimed is:

1. An image processing method for improving the three-dimensional display effect of blood vessels, wherein the image processing method comprises the following steps:

design an interpolation algorithm to preprocess the original data to obtain a preprocessed image based on the original image volume data before projection;

determine the blood vessel trend according to the preprocessed image, and eliminate isolated points, which specifically includes the following steps:

circulate each point in the preprocessed image, and judge whether the points to be identified are abnormal noise points one by one along three principal axes;

judge whether it is an abnormal point or not, and corresponding point is the abnormal point if the pixel value of the corresponding point is larger than the values of six adjacent points in three directions around X, Y, and Z, and filter out the abnormal point;

for each voxel, the vector formed with the surrounding 26 points is calculated to form the direction of blood vessel trend;

in the 13 directions of blood vessel trend, use the points in the two nearest neighbors to average respectively, so as to obtain 13 candidate values;

use the maximum of 13 candidate values as the value of the point to be filtered, then the filtering is completed;

perform image smoothing processing on the blood vessel trend to obtain a smooth image, which specifically includes the following steps:

judge the direction of the candidate blood vessel trend, and decide which direction is the most possible blood vessel trend;

traverse the direction of 13 blood vessel trend and calculate the absolute value err of each direction, which specifically includes the following steps:

calculate the average value my of the corresponding point and two neighboring points in the direction of a certain blood vessel trend;

calculate the absolute value of the difference between the corresponding point and the average value, which is the first absolute value err1 of the difference;

calculate the absolute value of the difference between two neighboring points, which is the second absolute value err2;

calculate the sum absolute value err of the first difference absolute value err1 and the second difference absolute value err2;

compare the absolute value err values in 13 directions, select the direction with the smallest absolute value err as the most possible blood vessel direction, and replace the value of the corresponding point with the average value my value in the corresponding direction to complete the smoothing function;

process the smooth image by a nonlinear change method to perform nonlinear enhanced display of blood vessels and suppress the background, which specifically includes the following steps:

the step of processing the smooth image by a nonlinear change method to perform nonlinear enhanced display of blood vessels and suppress the background specifically includes the following steps:

the formula of nonlinear transformation adopts gamma transformation, and the formula is as follows: $S=I^{\gamma}$ wherein, $\gamma>1$;

wherein, S is the transformed image, $\gamma$ is the variable that controls the transformation effect, and it is used to compress the background dark signal, and the larger $\gamma$ is, the more obvious the effect is;

or use the improved gamma transformation, the formula is $S=(1-\alpha I+\exp(-I)))^{\gamma}$, where S is the transformed image, I is the original image, $\alpha$ and $\gamma$ are the control variables, and the value of $\alpha$ less than 1 is selected; and $\gamma$ is greater than 1.

2. The image processing method for improving the three-dimensional display effect of blood vessels as claimed in claim 1, wherein, the step of designing an interpolation algorithm to preprocess the original data based on the original image volume data before projection specifically includes the following steps: interpolate the original image volume data into data with the same resolution in the layer direction, the row direction and the column direction.

3. The image processing method for improving the three-dimensional display effect of blood vessels as claimed in claim 1, wherein, the step of designing an interpolation algorithm to preprocess the original data based on the original image volume data before projection specifically includes the following steps:

respectively calculate that resolution of the original image volume data in three directions of row, column and layer;

judge whether to interpolate according to the actual resolutions of the original image volume data in three directions, and if so, select an appropriate interpolation direction and interpolation algorithm to preprocess the original image volume data.

4. The image processing method for improving the three-dimensional display effect of blood vessels as claimed in claim 1, wherein, the interpolation algorithm includes linear interpolation and cubic spline interpolation.

* * * * *